(12) United States Patent
Linn et al.

(10) Patent No.: US 8,902,045 B1
(45) Date of Patent: Dec. 2, 2014

(54) CONTROLLING ACCESS TO A COMPUTERIZED RESOURCE BASED ON AUTHENTICATION USING PULSE DATA

(75) Inventors: John Linn, Carlisle, MA (US); William M. Duane, Westford, MA (US); Yedidya Dotan, Tel Aviv (IL); Roy Hodgman, Wenham, MA (US)

(73) Assignee: EMC Corporation, Hopkinton, MA (US)

( * ) Notice: Subject to any disclaimer, the term of this patent is extended or adjusted under 35 U.S.C. 154(b) by 299 days.

(21) Appl. No.: 13/336,573

(22) Filed: Dec. 23, 2011

(51) Int. Cl.
*G08B 21/00* (2006.01)

(52) U.S. Cl.
USPC ......... 340/5.83; 340/5.53; 340/5.8; 340/5.81; 340/5.82; 382/115; 382/173

(58) Field of Classification Search
USPC ............. 340/5.52, 5.53, 5.8, 5.81, 5.82, 5.83; 382/115, 173; 707/100
See application file for complete search history.

(56) References Cited

U.S. PATENT DOCUMENTS

| | | | | |
|---|---|---|---|---|
| 2002/0149467 A1* | 10/2002 | Calvesio et al. | ............. | 340/5.52 |
| 2004/0133547 A1* | 7/2004 | Doi | .................. | 707/1 |
| 2005/0057339 A1* | 3/2005 | Ikehara et al. | ............... | 340/5.52 |
| 2007/0009139 A1* | 1/2007 | Landschaft et al. | .......... | 382/115 |
| 2009/0154809 A1* | 6/2009 | Fridrich et al. | ............... | 382/181 |
| 2009/0312647 A1* | 12/2009 | Kasama | ........................ | 600/483 |

OTHER PUBLICATIONS

Tsu-Wang (David) Shen, et al., "Implementation of a one-lead ECG human identification system on a normal population", Journal of Engineering and Computer Innovations, vol. 2(1), pp. 12-21, Jan. 2011.
Ming-Zher Poh, et al., "Non-contact, automated cardiac pulse measurements using video imaging and blind source separation", Optics Express, vol. 18, No. 10, May 10, 2010.

* cited by examiner

*Primary Examiner* — Mohammad Ghayour
*Assistant Examiner* — Mark Rushing
(74) *Attorney, Agent, or Firm* — BainwoodHuang (57) ABSTRACT

A technique performs an authentication operation using pulse and facial data from a user. The technique involves obtaining current pulse data from a user, and performing a comparison between the current pulse data from the user and expected pulse data for the user. The technique further involves generating an authentication result based on the comparison between the current pulse data and the expected pulse data. The authentication result may control user access to a computerized resource. Since such a technique uses pulse data, a perpetrator cannot simply submit a static image of a subject's face to circumvent the authentication process. In some arrangements, the technique involves obtaining videos of human faces and deriving cardiac pulse rates from the videos. For such arrangements, a standard webcam can be used to capture the videos. Moreover, such techniques are capable of factoring in circadian rhythms and/or aging adjustments to detect and thwart video replay attacks.

25 Claims, 5 Drawing Sheets

CONTROLLING ACCESS TO A COMPUTERIZED RESOURCE BASED ON AUTHENTICATION USING PULSE DATA

BACKGROUND

A conventional facial recognition system analyzes images of human faces. In particular, when the system receives a first image of a human face, the system measures the sizes, shapes, and/or positions of the subject's eyes, nose, mouth, and cheeks, among other features. The system then saves these face geometry measurements for later matching.

When the conventional facial recognition system receives a second image of a human face in the future, the system performs this measurement operation again. That is, in the same manner as for the first image, the system measures the sizes, shapes, and/or positions of eyes, nose, mouth, and cheeks of the subject's face, etc. in the second image. The system then matches these face geometry measurements taken from the second image against the saved face geometry measurements taken from the first image.

If the system determines that the face geometry measurements match within a predefined threshold of certainty, the system outputs a result indicating that the subject in the second image is the same as the subject in the first image. However, if the system determines that the face geometry measurements do not match within the predefined threshold of certainty, the system outputs a result indicating that the subject in the second image is not the same as the subject in the first image. Such results may be used to manage access to a protected asset such as a room, or an account on a computer.

SUMMARY

Unfortunately, there are deficiencies to the above-described conventional facial recognition system. In particular, the above-described conventional facial recognition system is highly susceptible to replay attacks. For example, suppose that a legitimate user utilizes such a system to control access to an account on a computer. That is, to login to the computer, the user allows the computer to capture an image of the user's face (e.g., via a webcam), measure the user's facial parameters, and match these measurements to previous face geometry measurements.

In such a situation, it is just as easy for a perpetrator to simply present a previously-obtained photograph of the user's face to the computer. In response, the computer would capture an image of the user's face from the photograph, measure the user's facial parameters from that image, and match these face geometry measurements to previous face geometry measurements. Accordingly, the computer would allow the perpetrator to login to the user's computer account.

In contrast to the above-described conventional facial recognition system which is highly susceptible to replay attacks, improved techniques are directed to performing authentication operations which use pulse data from users. Since such techniques require the presence of a pulse, a perpetrator cannot simply submit a photograph of a legitimate user's face to circumvent the authentication process. Rather, the photograph would provide no pulse and thus fail authentication. In some arrangements, the improved techniques involve the capture of videos of human faces and derivation of user-distinctive cardiac pulse waveforms from the videos (i.e., distinctive human pulse waveforms used for identification). In some arrangements, the authentication process includes both face recognition and pulse recognition as two difference factors used together. For such arrangements, standard webcams can be used to capture the videos. Moreover, such techniques are capable of factoring in pulse waveform variables such as changes in the pulse waveform during the day (e.g., circadian rhythm adjustments) and changes in pulse waveform over years (e.g., aging adjustments) to detect and thwart video replay attacks.

One embodiment is directed to a method of performing an authentication operation. The method includes obtaining current pulse data from a user, and performing a comparison between the current pulse data from the user and expected pulse data for the user. The method further includes generating an authentication result based on the comparison between the current pulse data and the expected pulse data. The authentication result is constructed and arranged to control user access to a computerized resource.

In some arrangements, the current pulse data is derived by performing a set of blind source separation operations on video data of the user's face. Here, motion-tolerant contact-free pulse-related waveform measurements can be extracted from the video data of the user's face. Such waveform measurements are then used as a biometric tool for human identification.

In some arrangements, the authentication operation is repeated over a connection session (e.g., while a user accesses a computer account, while a user remotely connects to an online bank account, and so on). In such continuous authentication arrangements, any unsuccessful authentication result or series of unsuccessful authentication results is capable of launching a remedial activity (e.g., challenging the user, terminating or disconnecting the user session, sending an alert message, etc.).

Other embodiments are directed to systems, apparatus, processing circuits, computer program products, and so on. Some embodiments are directed to various processes, electronic components and circuitry which are involved in performing authentication operations using human pulse data.

It should be understood that such improvements may leverage off of certain recent heart-related technology advances. For example, it has been determined that electrocardiogram (ECG) information is a possible biometric tool for human identification. Along these lines, there is a full-length research paper entitled "Implementation of one-lead ECG human identification system on a normal population", written by Tsu-Wang (David) Shen, Willis J Tompkins and Yu Hen Hu, and provided by the Journal of Engineering and Computer Innovations Vol. 2(1), pp. 12-21, January, 2011, the contents and teachings of which are hereby incorporated by reference in their entirety (hereinafter referred to as "the Shen reference").

Additionally, it has been determined that contact-free heart rate measurements which are motion-tolerant can be performed using video imaging and blind source separation. Along these lines, there is an article entitled "Non-contact, automated cardiac pulse measurements using video imaging and blind source separation", written by Ming-Zher Poh, Daniel J. McDuff, and Rosalind W. Picard, and provided by Optics Express, Vol. 18, No. 10, May 10, 2010, the contents and teachings of which are hereby incorporated by reference in their entirety (hereinafter referred to as "the Poh reference").

BRIEF DESCRIPTION OF THE DRAWINGS

The foregoing and other objects, features and advantages will be apparent from the following description of particular embodiments of the invention, as illustrated in the accompanying drawings in which like reference characters refer to the same parts throughout the different views. The drawings are not necessarily to scale, emphasis instead being placed upon illustrating the principles of various embodiments of the invention.

FIG. 1 is a block diagram of an environment for performing authentication operations using pulse data.

DETAILED DESCRIPTION

An improved technique is directed to performing an authentication operation which uses human pulse data. Since such a technique requires the presence of a pulse, a perpetrator cannot simply submit a photograph of a legitimate user's face to circumvent the authentication process. Rather, the photograph would provide no pulse and thus fail authentication. In some arrangements, the improved technique involves the capture of videos of human faces and the derivation of user-distinctive cardiac pulse waveform measurements from the videos. For such arrangements, a webcam or similar digital camera can be used to capture the videos. Moreover, such a technique is capable of factoring in waveform changes during the day (e.g., circadian rhythm adjustments), waveform changes over years (e.g., aging adjustments) to detect and thwart video replay attacks, and even changes in between.

Figure 1:
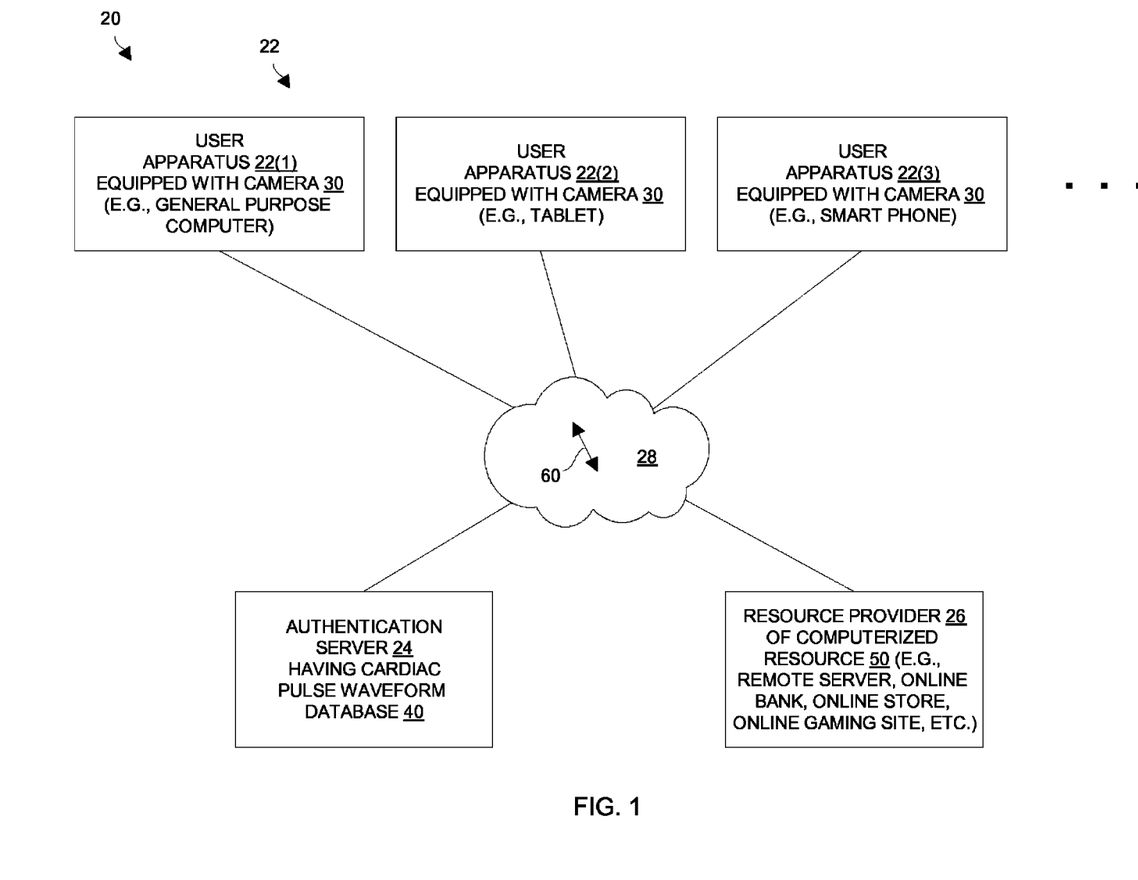

FIG. 1 shows an electronic environment 20 which performs authentication operations using human pulse data. The electronic environment 20 includes user apparatus 22(1), 22(2), 22(3), . . . (collectively, user apparatus 22), an authentication server 24, a resource provider 26, and communications medium 28.

Each user apparatus 22 is equipped with a camera 30 and is constructed and arranged to perform useful work on behalf of a user. With their respective cameras 30, each user apparatus 22 has the ability to capture video. For example, the user apparatus 22(1) may be a general purpose computer with a webcam. Similarly, the user apparatus 22(2) may be a tablet with a built-in digital camera. Additionally, the user apparatus 22(3) may be a smart phone with a built-in camera, and so on. With such cameras 30, the user apparatus 22 are able to capture detailed moving color video input (i.e., sequences of video frames) of human faces for use in authentication.

The authentication server 24 includes a cardiac pulse waveform database 40. The authentication server 24 is constructed and arranged to store cardiac pulse waveform data from multiple users in the cardiac pulse waveform database 40, and to perform authentication operations using the cardiac pulse waveform data (e.g., biometric similarity evaluations). In some arrangements, the cardiac pulse waveform data includes detailed representations of actual human pulse waveforms and perhaps even the captured video itself (e.g., to accommodate future waveform matching techniques). In other arrangements, the cardiac pulse waveform data includes only waveform measurements of particular parts of the actual human pulse waveforms (e.g., to optimize back-end processing and minimize storage). In yet other arrangements, the cardiac pulse waveform data includes both detailed representations of actual human pulse waveforms as well as waveform measurements of particular parts of the actual human pulse waveforms (e.g., to provide greatest flexibility).

The resource provider 26 provides each user apparatus 22 with access to one or more computerized resources 50 following successful user authentication through that user apparatus 22. An example of a suitable resource provider 26 is a data storage array which provides secure access to files, directories, volumes, LUNs, etc. Another example of a suitable resource provider 26 is a web server which provides secure access to various web pages. Yet another example of a suitable resource provider 26 is a server which provides secure user account and/or transactional access such as that for an online banking site, an online store, an online gaming site, and so on. Other types of resource providers are suitable for use as well.

The communications medium 28 connects the various components of the electronic environment 20 together to enable these components to exchange electronic signals 60 (e.g., see the double arrow 60). At least a portion of the communications medium 28 is illustrated as a cloud to indicate that the communications medium 28 is capable of having a variety of different topologies including backbone, hub-and-spoke, loop, irregular, combinations thereof, and so on. Along these lines, the communications medium 28 may include copper-based devices and cabling, fiber optic devices and cabling, wireless devices, combinations thereof, etc.

During operation, a user of a user apparatus 22 allows video of his or her face to be captured by the camera 30 of that user apparatus 22. The processing circuitry of the electronic environment 20 then obtains current pulse data from this video input, performs a comparison between the current pulse data and expected pulse data, and generates an authentication result based on the comparison between the current pulse data and the expected pulse data. The authentication result (e.g., a successful or unsuccessful authentication value, a weight/score, a partial result or factor to be combined with other factors, etc.) controls user access to the computerized resource 50.

In some arrangements, the authentication server 24 receives the video input directly from the user apparatus 22 (i.e., the user attempts to authenticate directly with the authentication server 24) or indirectly through the remote protected resource 26 (i.e., the user attempts to authenticate with the remote protected resource 26 which then delegates the authentication task to the authentication server 24). In these arrangements, the authentication server 24 performs a set of blind source separation operations on the video input to identify a current pulse waveform of the user. Those of skill in the art will appreciate that such blind source separation operations enables convenient separation of the current pulse waveform from other signals mixed within the video input. The authentication server 24 then retrieves an expected pulse waveform for the user from the cardiac pulse waveform database 40. The authentication server 24 then compares measurements of the current pulse waveform to measurements of the expected pulse waveform to determine whether the user is authentic or an imposter. Along these lines, it should be understood that each pulse waveform has particular parts which are recognizable and measurable (e.g., amplitude, timing, shape, etc. of the P wave, the T wave, and so on) in order to determine a level of similarity between such patterns. A detailed discussion of the distinctive aspects of a human electrocardiogram (ECG) is provided in the Shen reference. In one arrangement, the result of the waveform measurement comparison is included as a factor in risk-based authentication. In another arrangement, the result of this comparison is included as a factor in multi-factor authentication. In still another arrangement, this result operates as the final authentication result (i.e., a simple binary yes/no, not risk based, not multi-factor).

In some arrangements, the user apparatus 22 which captures the video input is further tasked with performing the set of blind source separation operations on the video input to identify the current pulse waveform of the user. In these arrangements, the user apparatus 22 then sends a computerized representation of the current pulse waveform of the user to the authentication server 24 which, in turn, completes the authentication process. Such offloading of the blind source separation operations from the authentication server 24 to the user apparatus 22 lowers bandwidth through the communications medium 28 and consumes less processing resources at the authentication server 24.

In other arrangements, each user apparatus 22 not only performs the set of blind source separation operations on the video input, but also locally stores a representation or measurements of the expected pulse waveform for the user as well as performs the comparison operation. In these arrangements, each user apparatus 22 essentially operates as its own localized authentication server 24 to perform the entire authentication process including the comparison of waveform measurements.

It should be understood that various other modifications can be made to create other arrangements. For instance, in some arrangements, the computerized resource 50 resides locally within the user apparatus 22. Additionally, the electronic environment 20 is well-suited to support various combinations of these arrangements. Further details will now be provided with reference to FIG. 2.

Figure 2:
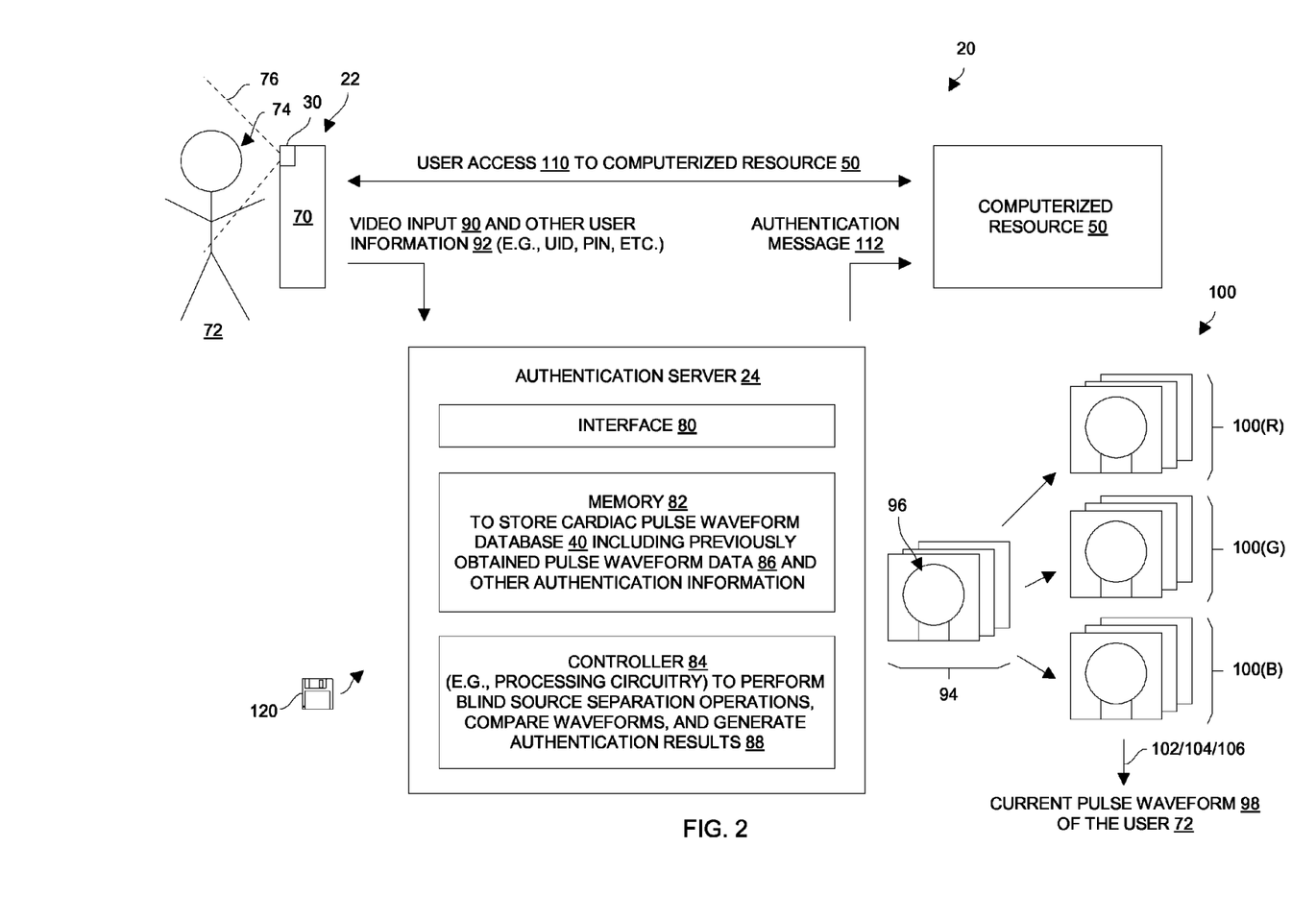
FIG. 2 is a block diagram of particular details of the environment of FIG. 1 during an authentication process.

FIG. 2 shows particular details of the electronic environment 20 during the authentication process. In the scenario illustrated in FIG. 2, the authentication server 24 is external to the user apparatus 22, and the authentication server 24 performs authentication taking captured video as input.

As shown, the user apparatus 22 includes a camera 30 and processing circuitry 70 for performing useful work. When a user 72 operates the user apparatus 22, the user 72 positions his or her face 74 within a field of view 76 of the camera 30. The processing circuitry 70 then buffers and transmits captured video from the camera 30 (or alternatively performs certain local processing before transmitting processed data) to the authentication server 24. Such a transmission may take place over a network (e.g., see the communications medium 28 in FIG. 1).

As further shown in FIG. 2, the authentication server 24 includes an interface 80, memory 82 and a controller 84. The interface 80 allows the authentication server 24 to communicate with other components of the electronic environment 20 through the communications medium 28 (also see FIG. 1). The memory 82 stores the cardiac pulse waveform database 40 which includes previously obtained pulse waveform data 86 (e.g., representations of human pulse waveforms themselves, pulse waveform measurements, combinations thereof, etc.) as well as other data (e.g., user information). The controller 84 carries out authentication operations by performing blind source separation operations to obtain current pulse waveforms, comparing the current pulse waveforms to expected pulse waveforms represented by the pulse data 86 stored in the database 40, and generating authentication results 88 to control access to the computerized resource 50.

Along these lines, suppose that the user 72 wishes to authenticate with the authentication server 24. It is assumed that the user has previously completed a setup process to store pulse waveform data 86 (i.e., representations of previous pulse waveforms) in the cardiac pulse waveform database 40 of the authentication server 24

To begin the authentication process, the user provides current video input 90 from the camera 30 and other user information 92 to the authentication server 24 (also see the electronic signals 60 in FIG. 1). For example, the user may communicate with the authentication server 24 directly as part of a front-end authentication process prior to attempting to access the computerized resource 50. Alternatively, the user may communicate with other circuitry to authenticate (e.g., the resource provider 26 in FIG. 1) and, in turn, that circuitry communicates with the authentication server 24 to initiate the authentication process.

In either situation, the current video input 90 from the user apparatus 22 includes a series of video frames 94 which includes images of the user's face 96. The other user information 92 may include a user identifier (e.g., a username) to indicate who the user claims to be and perhaps other authentication factors such a password or personal identification number (PIN), a one-time passcode (OTP), date and time information, specific software and hardware information, ISP information, other authentication factors, combinations thereof, and so on.

Next, the authentication server 24 performs an authentication operation which considers a current pulse waveform 98 of the user 72. To obtain the current pulse waveform 98 of the user 72, the controller 84 performs a cardiac pulse recovery operation on the series of video frames 94. Along these lines, the controller 84 detects a region of interest (ROI) within the series of video frames 94 (e.g., using a standard face tracker). The controller 84 then decomposes the ROI into individual color channels 100 (e.g., a red color channel 100(R), a green color channel 100(G), and a blue color channel 100(B)) and spatially averages the ROI to obtain raw RGB traces 102. The controller 84 then applies Independent Component Analysis (ICA) 104 on the RGB traces 102 to recover multiple independent source signals 106. From the independent source signals 106, the controller 84 acquires the current pulse waveform 98 of the user 72. Additional information regarding such a process or a similar process and embellishments thereto can be found in the Poh reference. Other mechanisms may be suitable for use as well.

It should be understood that this technique of obtaining the current pulse waveform 98 of the user 72 from the series of video frames 94 captured by the camera 30 of the user apparatus 22 is non-invasive to the user 72. In particular, there is no physical contact with the user required. Rather, the user 72 is physically separated from the camera 30 and simply moves his or her face 74 into the viewing field 76 of the camera 30. Moreover, there is no special hardware required. Rather, the technique simply leverages off of the existing video capture circuitry of the user apparatus 22.

Once the controller 84 of the authentication server 24 has obtained the current pulse waveform 98 of the user 72, the controller 84 compares the current pulse waveform 98 to an expected pulse waveform represented by pulse data 86 for the user 72. It should be understood that the effectiveness of this comparison is based on the individual identifying characteristics of one human pulse to another, thus enabling human pulse waveforms to operate as a means of identifying users among each other, e.g., as explained in the Shen reference.

To obtain the expected pulse waveform represented by the pulse data 86, the controller 84 retrieves the pulse data 86 for the user from the cardiac pulse waveform database 40 stored in the memory 82. In some arrangements, one or more entries are retrieved from the database 40 based on the other user identification information 92 which accompanies the current video input 90. As will be explained shortly, the controller 84 is capable of making pulse waveform adjustments prior to performing the comparison (e.g., averaging particular waveform measurements from multiple entries of the pulse data 86, correcting based on circadian rhythms, compensating for aging since the pulse data 86 was taken, and so on).

Based on the comparison between the current pulse waveform 98 and the expected pulse waveform based on the pulse data 86 from the database 40, the controller 84 generates an authentication result 88 which is then used to control access 110 to the computerized resource 50. For example, the controller 84 may include the authentication result 88 as a factor in a larger authentication process (e.g., multi-factor or risk-based authentication), the outcome of which is sent to the resource provider 26. Alternatively, the controller 88 may bundle the authentication result 88 within an authentication message 112 for use by the resource provider 26 and/or the user apparatus 22 to allow access or deny access to the computerized resource 50 (e.g., a resource of the resource provider 26 which is external to the user apparatus 22, a resource within the user apparatus 22, combinations thereof, etc.).

At this point, it should be understood that the controller 84 of the authentication server 24 is capable of being implemented in a variety of ways including via one or more processors running specialized software, application specific ICs (ASICs), field programmable gate arrays (FPGAs) and associated programs, discrete components, analog circuits, other hardware circuitry, combinations thereof, and so on. In the context of one or more processors running specialized software, a computer program product 120 is capable of delivering all or portions of the software. The computer program product 120 has a non-transitory (or non-volatile) computer readable medium which stores a set of instructions which controls one or more operations controller 84. Examples of suitable computer readable storage media include tangible articles of manufacture and apparatus which store instructions in a non-volatile manner such as CD-ROM, flash memory, disk memory, tape memory, and the like. Further details will now be provided with reference to FIGS. 3 and 4.

Figure 3:
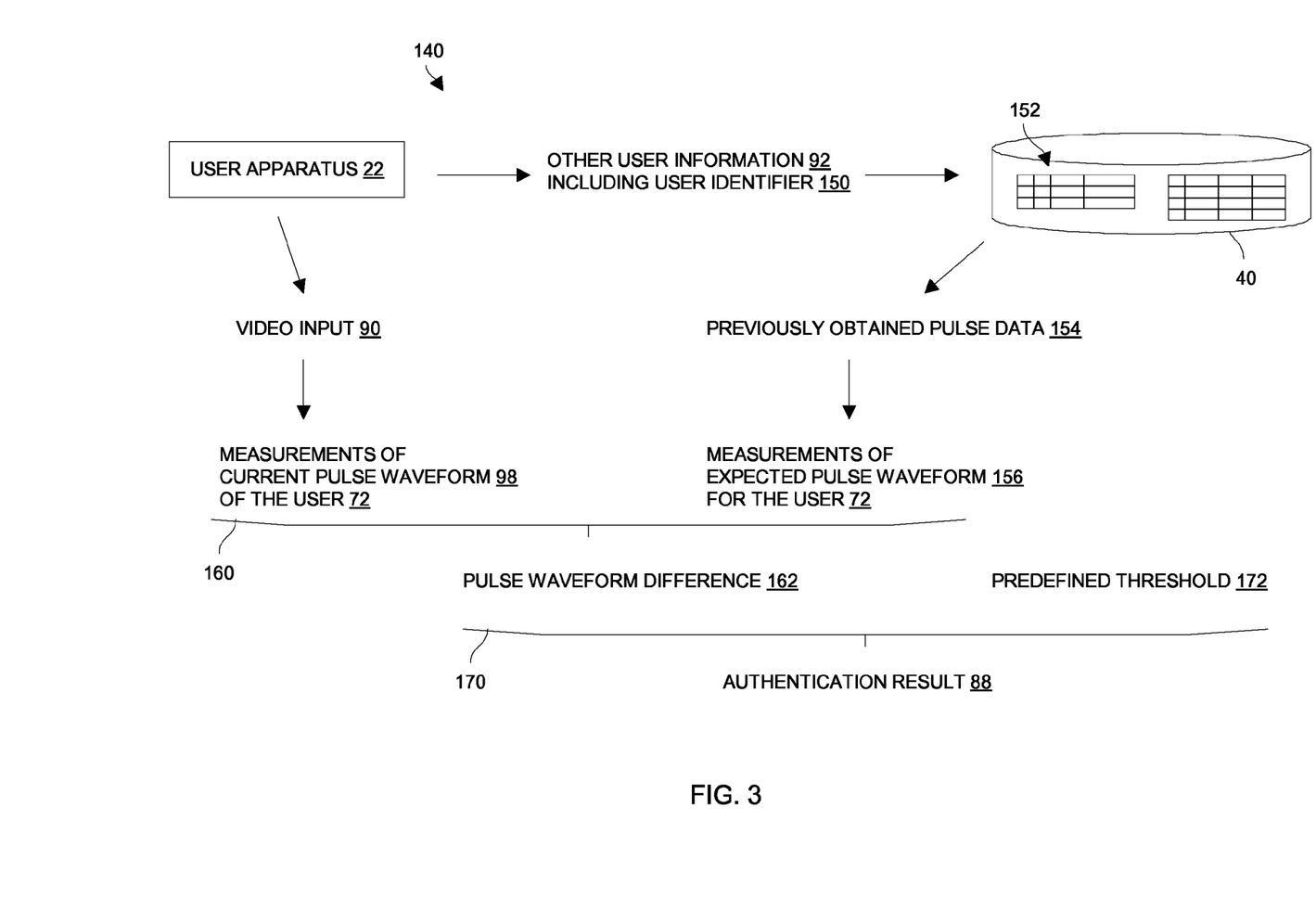
FIG. 3 is a block diagram of particular details of a general authentication operation which is performed by control circuitry.
Figure 4:
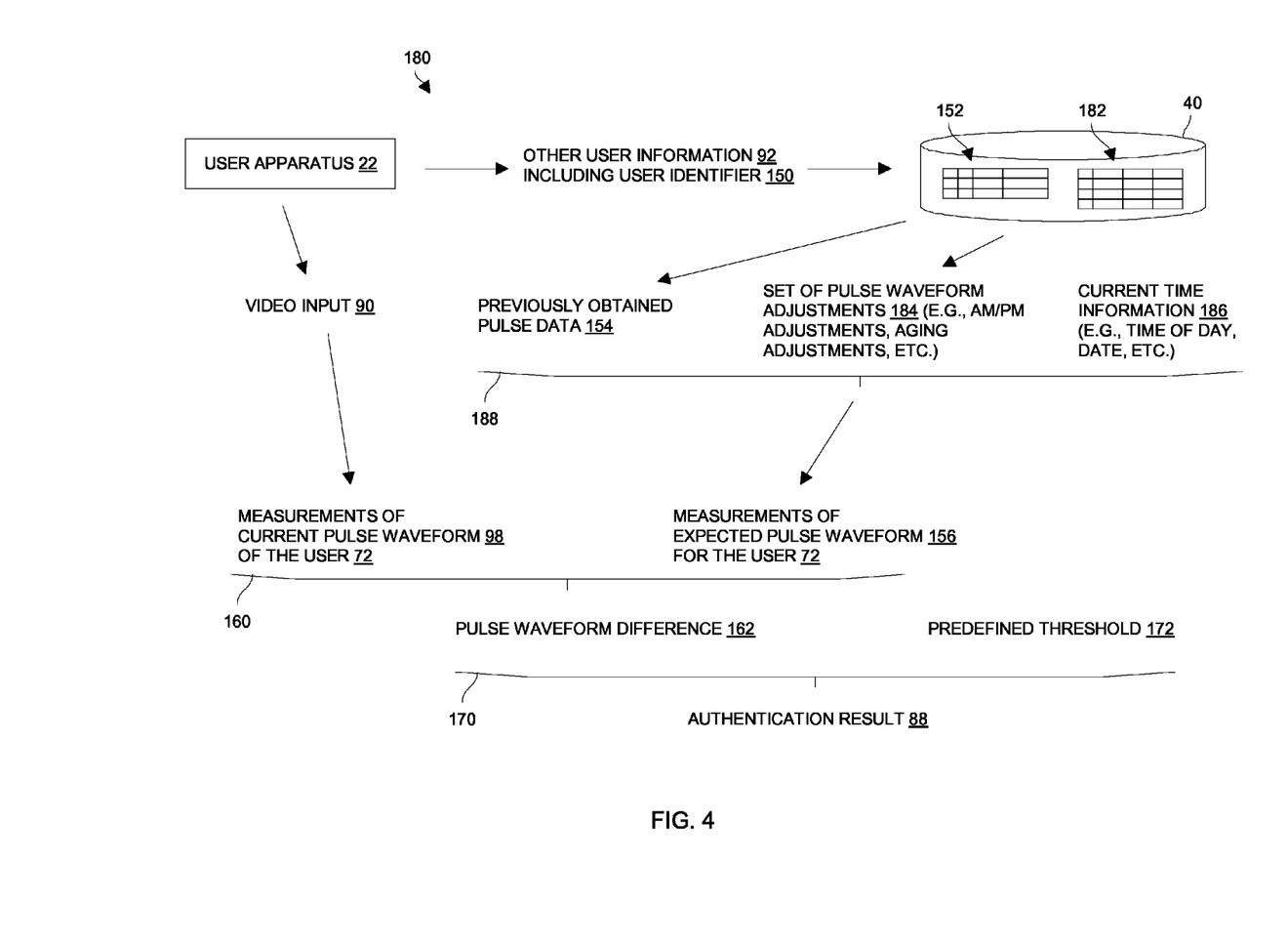
FIG. 4 is a block diagram of particular details of an advanced authentication operation which is performed by control circuitry.

FIGS. 3 and 4 show example authentication operations which are capable of being performed by the controller 84 to detect and thwart video replay attacks. In particular, FIG. 3 shows a general authentication operation 140 which is capable of being performed by the controller 84 of the authentication server 24. FIG. 4 is an advanced authentication operation 180 which is capable of being performed by the controller 84 of the authentication server 24.

As shown for the general authentication operation 140 in FIG. 3, the user apparatus 22 provides the video input 90 from which the controller 84 derives the measurements of the current pulse waveform 98 of the user 72. In some arrangements, the controller 84 performs video imaging and blind source separation operations on the video input 90 to obtain the measurements of the current pulse waveform 98 (e.g., also see FIG. 2 and the Poh reference).

Additionally, the user apparatus 22 further is equipped to provide other user information 92 including a user identifier 150 which identifies who the user 72 claims to be among multiple users 72. The controller 84 then accesses the entries 152 within the cardiac pulse waveform database 40, and retrieves previously obtained pulse data 154 of the user 72 (also see the pulse data 86 in FIG. 2). In some arrangements, each pulse data entry 152 includes a user identifier 150 to identify a user 72, pulse data 86 of that user 72, and a timestamps to identify times of day and dates relating to the pulse waveform, among other things. For example, such timestamps may identify the date/time the waveform was collected, the date/time the waveform was stored, and/or the date/time the waveform was analyzed, among other things. From this collective information (i.e., the pulse data 154), the controller 84 generates a set of measurements for an expected cardiac pulse waveform 156 for the user 72. In some arrangements, the controller 84 combines previous waveform measurements to generate the expected cardiac pulse waveform 156.

As illustrated by the bracket 160, the controller 84 then computes a pulse waveform difference 162 from (i) the measurements of the current pulse waveform 98 of the user 72 from the user apparatus 22 and (ii) the measurements of the expected pulse waveform 156 for the user 72 from the database 40. The pulse waveform difference 162 is an objective indicator of how closely the current pulse waveform 98 matches the expected pulse waveform 156 from a pattern matching perspective. That is, this pulse waveform difference 162 (e.g., a set of individual differences, an aggregation or summation of individual differences, a weighted score, etc.) serves as an indication of the likelihood that the current pulse waveform 98 is not that of the legitimate user as identified by the user identifier 150 where the larger the pulse waveform difference 162, the greater the likelihood that the user 72 is not legitimate.

It should be understood that, as is commonly the case with biometrics, the newly measured pulse characteristics may not exactly match previously measured pulse characteristics. Rather, some difference is to be expected when the legitimate user authenticates. Nevertheless, as in other forms of biometric authentication, successful match criteria requires the difference (in this case, the pulse waveform difference 162) to fall within a predefined threshold as explained further below.

As illustrated by the bracket 170, the controller 84 then compares the pulse waveform difference 162 to a predefined threshold (or set of thresholds) 172 to generate an authentication result 88. For example, in some arrangements, if the pulse waveform difference 162 is less than (or equal to) the predefined threshold 172, the controller 84 considers the user 72 to be legitimate and outputs, as the authentication result 88, a value indicating successful authentication. In these arrangements, if the pulse waveform difference 162 is greater than the predefined threshold 172, the controller 84 considers the user 72 to be an imposter and outputs, as the authentication result 88, a value indicating unsuccessful authentication based on pulse waveform.

In some arrangements, the predefined threshold 172 is initially set to a default setting at authentication server startup time. Later, an administrator of the authentication server 24 is able to change the default setting (e.g., lower the predefined threshold 172 to increase protection of the computerized resource 50, increase the predefined threshold 172 to lower protection of the computerized resource 50, etc.).

In some arrangements, the authentication server 24 maintains a global predefined threshold 172 for use during authentication operations of multiple users 72. In other arrangements, the authentication server 24 maintains a respective predefined threshold 172 for each user 72.

It should be understood that these predefined thresholds 172 may be changed over time. For example, the predefined thresholds 172 may be adjusted by external criteria such as automated procedures which incorporate feedback from service centers which identify false negatives.

Additionally, it should be understood that the authentication result 88 is capable of directly controlling access to the computerized resource 50 (FIGS. 1 and 2). In particular, in some arrangements, the controller 84 grants access to the computerized resource 50 when the authentication result 88 has the successful authentication value, and denies access to the computerized resource 50 when the authentication result 88 has the unsuccessful authentication value.

However, in other arrangements, the authentication result 88 is simply one of multiple factors under consideration as the controller 84 controls access to the computerized resource 50. For example, the controller 84 may include the authentication result 88 as a factor in traditional multi-factor authentication where other factors include a PIN, an OTP, and so on. As another example, the controller 84 may include the authentication result 88 as one of many factors (e.g., geo-location, time of day, etc.) as part of the generation of a risk score in risk-based authentication. Other alternatives are suitable for use as well.

As shown in FIG. 4, the controller 84 is capable of performing an advanced authentication operation 180 rather than the general authentication operation 140 of FIG. 3. The advanced authentication operation 180 is similar to the general authentication operation 140, but the advanced authentication operation 180 is capable of accommodating subtle changes in human pulse waveforms over time (e.g., based on time of day, based on aging, etc.).

Along these lines, the cardiac pulse waveform database 40 is capable of storing enhanced human pulse waveform information 182 which enables the controller 84 to derive a set of pulse waveform adjustments 184. Such a set of pulse waveform adjustment 184 enables the controller 84 of the authentication server 24 to factor in current time information 186 (e.g., time of day, amount of time elapsed since last authentication date, etc.) and identify replay video attacks such as an imposter trying to replay a video of the legitimate user taken in the morning during an authentication operation in the evening, or a video of the legitimate user taken several years ago.

Such a set of pulse waveform adjustments 184 may include user-specific adjustments for the time of day (e.g., circadian rhythm parameters). For example, suppose that the controller 84 has collected enough previous pulse waveform data in the cardiac pulse waveform database 40 from the legitimate user that the controller 84 has determined that the legitimate user's pulse waveform is slightly different in shape in the evening (e.g., due to improved cardiac efficiency later in the day). To compensate for this circadian-style change in pulse waveform during the day, the controller 84 is capable of performing an adjustment operation 188 (shown by the bracket 188) to generate the measurements of the expected pulse waveform 156 for the user 72. The adjustment operation 188 may involve increasing (or decreasing) one particular measurement or multiple measurements. For instance, the controller 84 can adjust a nominal expected pulse waveform 156 by a morning-side set of adjustment factors for authentication operations in the morning (A.M.), and by an evening-side set of adjustment factors for authentication operations in the evening (P.M.).

Alternatively, the adjustment operation 188 may involve ignoring certain previously obtained measurements of cardiac pulse waveforms obtained from the user during times of days that were outside a particular time of day (e.g., querying the database 40 for only evening user pulse data 86 if authentication is performed during the evening, etc.). Since people have different biorhythms, such operation enables the authentication server 24 to improve its ability to identify legitimate users as well as imposters.

As another example, suppose that the controller 84 has collected previous pulse data 86 in the cardiac pulse waveform database 40 from the legitimate user, but that the previous pulse data 86 was acquired several years ago. In some arrangements, the controller 84 is configured to make waveform adjustments 184 which predict a specific change (e.g., pregnancy, recovery from an injury, aging, etc.). Along these lines, suppose that the cardiac pulse waveform database 40 includes the user's age (e.g., see the enhanced human pulse waveform information 182) and has determined that the user's pulse waveform should have changed in a particular manner (e.g., due to age, due to a unique heart condition or recovery from the condition, etc.). In these situations, the controller 84 is capable of compensating for this age-style change in the pulse waveform since the previous pulse waveform data was acquired. Again, the bracket 188 represents an adjustment operation 188, i.e., increasing or decreasing one or more measurements for an expected cardiac pulse waveform to accommodate for the elapsed time since the earlier pulse waveform data was obtained.

In other arrangements, the controller 84 is configured to adjust the predefined threshold 172 to factor in decay after such a long period of time. For example, if the current pulse data is a precise match or too close to the previous pulse data 86 acquired several years ago, the controller 84 may deem this to be a replay attack.

In yet other arrangements, the controller 84 is configured to trigger acquisition of new reference data. That is, due to the large amount of time that has passed, the controller 84 invalidates the previous pulse data 86 acquired several years ago and collects new data for future authentication.

It should be understood that other modifications can be made as well. For example, geo-location may be factored into the adjustments. In particular, if the setting is a doctor's office or an exercise facility, adjustments may be made to slightly modify the expected pulse waveform in a particular manner or broaden the acceptable uncertainty. due to anxiety, exercise, caffeine, and so on. Alternatively, if the setting is a passive location, adjustments may be made to slightly modify the expected pulse waveform in an opposite manner. Such adjustments are purposeful in order to detect replay attacks from imposters. Further details will now be provided with reference to FIG. 5.

Figure 5:
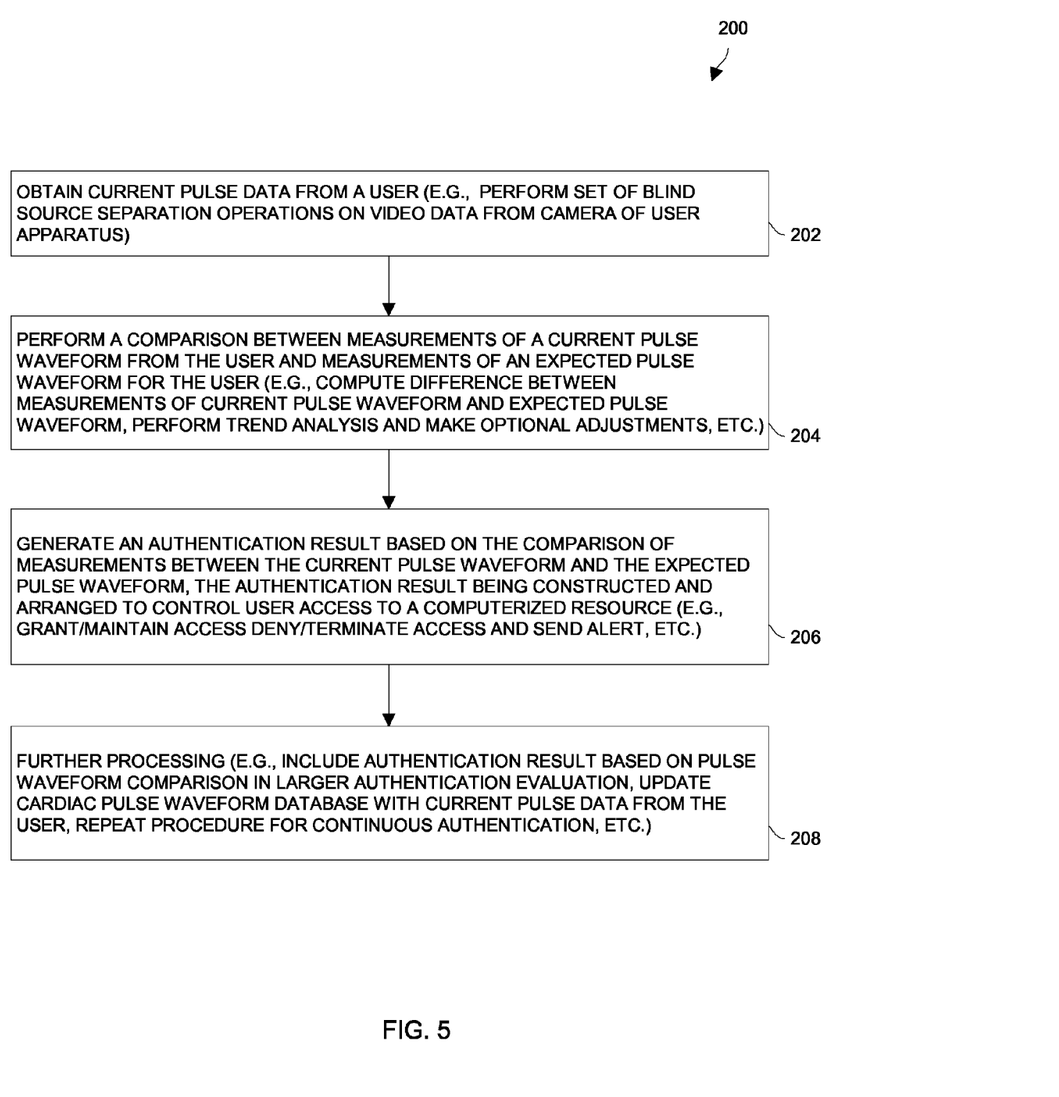
FIG. 5 is a flowchart of a procedure which is performed by circuitry of the environment of FIG. 1 when performing authentication operations using pulse data.

FIG. 5 is a flowchart of a procedure 200 which is performed by the controller 84 of the authentication server 24 when performing authentication operations using pulse data. It should be understood that, in some systems, the user may provide an assertion of identity (e.g., a username to a login prompt), and the system evaluates the face and pulse to the asserted identity. However, other systems perform a search based on the facial data, then further guarantees that it is the right face based on the pulse data.

In step 202, the controller 84 obtains current pulse data from a user 72 of a user apparatus 22 (also see FIG. 1). The user 72 may wish to authenticate in order to remotely access a computerized resource 50 on a resource provider 26 such as a remote server or online store. Alternatively, the computerized resource 50 may reside locally on the user apparatus 22 (e.g., the user attempting to login or unlock a computer, tablet or smart phone).

In step 204, the controller 84 performs a comparison between the current pulse data from the user and expected pulse data for the user. In some arrangements, the controller 84 derives measurements of a current pulse waveform 98 of the user 72 based on video input 90 from a camera 30 of the user apparatus 22 in a non-contact manner (also see FIG. 2). Along these lines, the controller 84 performs a set of blind source separation operations and ICA on the video input 90 which captures the user's face 74.

Additionally, the controller 84 obtains measurements of an expected cardiac pulse waveform 156 for the user 72 based on previously obtained pulse data 86 of the user 72 which is stored in entries 152 of the cardiac pulse waveform database 40 (FIG. 3). In some arrangements, the controller 84 adjusts the measurements of the expected cardiac pulse waveform 156 based on a set of pulse waveform adjustments 184 such as circadian rhythms to factor in changes in pulse waveforms during a 24-hour window, and aging trends to factor in changes in pulse waveforms over an extended amount of time (e.g., years).

In step 206, the controller 84 generates an authentication result 88 based on the comparison between the current pulse data and the expected pulse data. In particular, the controller 84 computes differences in measurements of a current pulse waveform 98 of the user 72 and an expected pulse waveform 156 for the user 72. The authentication result 88 is constructed and arranged to control user access to the computerized resource 50.

In step 208, the controller 84 performs further processing. For example, in some arrangements, the authentication result 88 is incorporated by the controller 84 into a larger authentication outcome such as a multi-factor authentication operation or a risk-based authentication operation. Additionally, if authentication is successful, the controller 84 may update the cardiac pulse waveform database 40 to include the current pulse data within a new entry 152, maintain access if the user 72 had previously successfully authenticated during a continuous authentication session, and so on. However, if authentication is unsuccessful, the controller 84 may perform a remedial action such as send an alert to an administrator of the electronic environment 20, deny access to the computerized resource 50, terminate access if the user 72 had previously successfully authenticated during a continuous authentication session, provide a different challenge to the user 72, and so on.

In some arrangements, the controller 84 performs authentication in a continuous manner. For example, the user 72 may be participating in an online meeting and thus provide a continuous video stream as the video input 90 for continuous authentication. In these arrangements, step 208 proceeds back to step 202 to repeat the procedure 200 on new pulse data at set intervals (e.g., every minute, every five minutes, etc.).

As described above, improved techniques are directed to performing authentication operations which use pulse data from a user 72. Since such techniques require the presence of a human pulse, a perpetrator cannot simply submit a photograph of a legitimate user's face to circumvent the authentication process. Rather, the photograph would provide no pulse and thus fail authentication. In some arrangements, the improved techniques involve the capture of videos of human faces and derivation of user-distinctive cardiac pulse waveforms from the videos (i.e., human pulse waveforms used for identification). For such arrangements, standard webcams can be used to capture the videos. Moreover, such techniques are capable of factoring in pulse waveform trends such as changes in pulse waveform during the day (e.g., circadian rhythm adjustments) and changes in pulse waveform over years (e.g., aging adjustments) to detect and thwart video replay attacks.

While various embodiments of the invention have been particularly shown and described, it will be understood by those skilled in the art that various changes in form and details may be made therein without departing from the spirit and scope of the invention as defined by the appended claims.

For example, the authentication process was described above as being primarily performed remotely within the authentication server 24 by way of example only. In other arrangements, the authentication process is performed elsewhere such as locally within a user apparatus 22 (e.g., for local login access), or at the resource provider 26 (e.g., when the resource provider maintains oversight/responsibility for authentication).

Additionally, it should be understood that the authentication result 88 may be combined with other security mechanisms. For example, the same video input 90 which is used to derive the current pulse waveform 98 of the user 72 includes other information such as facial geometries, facial features and facial component distances for processing by a facial recognition mechanism. Also, other artifacts (e.g., mouth movement, accompanying noise, lighting, background data, etc.) may be used as factors in combination with pulse waveform derivation for vitality detection, voice identification, location identification, and so on.

Furthermore, it should be understood that a variety of remedial activities are available in the event the authentication result 88 indicates unsuccessful authentication. For example, the controller 84 may terminate an existing user session, or deny access to the computerized resource. Alternatively, the controller 84 may issue challenges for other information, and so on.

Moreover, in some arrangements, the cardiac pulse waveform database 40 (e.g., see FIGS. 3 and 4) is part of a larger authentication database such as a multi-factor authentication database, or a risk-based or adaptive authentication database. In other arrangements, the cardiac pulse waveform database 40 is maintained separately and independently.

In some arrangements, the system provides continuous authentication with a grace period. For example, suppose that a legitimate user performs initial authentication on the user's workstation, and then leaves or stops facing the camera. In these arrangements, the system continues to accept user input for the grace period. However, once the grace period is exceeded, the system locks out further user input automatically. Accordingly, if an imposter were to subsequently sit down at the user's workstation, the imposter would not be able to access the resource.

Additionally, it should be understood that the above-described video input processing technique is one particular way of obtaining a pulse waveform from video input. However, other techniques can be used as well. Along these lines, decomposing a region of interest (ROI) into individual color channels, spatially averaging the ROI to obtain raw traces, and applying Independent Component Analysis (ICA) was provided by way of example as a way to recover multiple independent source signals. Additionally, blind source separation operations were described by way of example only as being suitable for use when separating the current pulse waveform from other signals, artifacts, noise, etc. mixed within the video input. It should be understood that other computational operations may be suitable for use as well to obtain the pulse waveform from the video input.

Furthermore, it should be understood that the human face was described as the particular body part from which to obtain pulse waveforms. Since the human face may be captured for other purposes (e.g., liveliness testing, facial recognition, etc.), the same data is conveniently available for pulse waveform extraction. However, in other arrangements, a different body part is analyzed for pulse waveform extraction. For example, areas such as the wrist, neck, and so on, are parts of the body that express pulse in readily visible form. Additionally, while devices such as fingerprint scanners and eye scanners obtain images of other body parts for other forms of authentication (e.g., fingerprint recognition and retina recognition), such scanners can be used as a vehicle to obtain pulse data concurrently.

Additionally, it should be understood that although a typical authentication transaction may involve entering a username (e.g., before a password), other arrangements involve biometric identification as a means to generate a user identifier 150. In these arrangements, biometric identification (e.g., based on the user's face) avoids the need to enter a username. The cardiac pulse waveform database 40 is then queried using the generated user identifier 150. Such modifications and enhancements are intended to belong to various embodiments of the invention.

What is claimed is:

1. A method of performing an authentication operation, the method comprising:
   receiving an electronic input signal from an electronic input device to take current pulse data from a user;
   performing a comparison between the current pulse data from the user and expected pulse data for the user; and
   generating an authentication result based on the comparison between the current pulse data and the expected pulse data, the authentication result being constructed and arranged to control user access to a computerized resource;
   wherein performing the comparison between the current pulse data from the user and the expected pulse data for the user includes:
      retrieving previously obtained cardiac pulse data of the user from a cardiac pulse waveform database which stores multiple pulse data entries, each pulse data entry including (i) pulse data and (ii) a timestamp,
      identifying a set of pulse waveform adjustments from the pulse data entries, and
      generating, as at least part of the expected pulse data, measurements of an expected cardiac pulse waveform for the user based on (i) pulse data of particular pulse data entries stored in the cardiac pulse waveform database, (ii) the set of pulse waveform adjustments, and (iii) current time information.

2. The method as in claim 1 wherein the electronic input device is a digital camera;
   wherein receiving the electronic input signal from the electronic input device includes capturing video data while the user's face is within a field of view of the digital camera; and
   wherein deriving the current pulse data from the electronic input signal includes performing a set of computational operations on the video data to identify, as at least part of the current pulse data, a current cardiac pulse waveform of the user from the user's face.

3. The method as in claim 1 wherein retrieving the previously obtained cardiac pulse data of the user from the cardiac pulse waveform database includes:
   receiving a user identifier in response to an authentication request submitted by the user, the user identifier distinguishing the user among multiple users,
   querying the cardiac pulse waveform database based on the user identifier to obtain the particular pulse data entries.

4. The method as in claim 1 wherein generating the authentication result based on the comparison between the current pulse data and the expected pulse data includes:
   outputting, as the authentication result, a risk score based on a set of risk factors, a result of the comparison between the current pulse data and the expected pulse data being one of the set of risk factors.

5. The method as in claim 4, further comprising:
   granting access to the computerized resource when the risk score exceeds a predefined threshold, and
   denying access to the computerized resource when the risk score does not exceed the predefined threshold.

6. The method as in claim 1 wherein identifying the set of pulse waveform adjustments from the pulse data entries includes calculating a morning-side set of pulse waveform adjustment factors and an evening-side set of pulse waveform adjustment factors that is different than the morning-side set of pulse waveform adjustment factors;
   wherein the current time information includes a current time of day; and
   wherein generating the measurements of the expected cardiac pulse waveform for the user includes providing measurements of a nominal expected pulse waveform based on the particular pulse data entries stored in the cardiac pulse waveform database and adjusting the measurements of the nominal expected pulse waveform based on the morning-side and evening-side sets of adjustment factors and the current time of day.

7. The method as in claim 1 wherein identifying the set of pulse waveform adjustments from the pulse data entries includes calculating a set of adjustment factors based on an age of the user;
   wherein the current time information includes a current date; and
   wherein generating the measurements of the expected cardiac pulse waveform for the user includes providing measurements of a nominal expected pulse waveform based on the particular pulse data entries stored in the cardiac pulse waveform database and adjusting the measurements of the nominal expected pulse waveform based on the set of adjustment factors and an amount of time that has elapsed between a time associated with the particular pulse data entries and the current date.

8. The method as in claim 1 wherein retrieving the previously obtained cardiac pulse data of the user from the cardiac pulse waveform database includes:
   based on the user's face, performing a biometric identification operation to generate a user identifier, and
   querying the cardiac pulse waveform database based on the generated user identifier to obtain the particular pulse data entries.

9. The method as in claim 1, further comprising:
   establishing an access session in which the user accesses the computerized device in response to the authentication result indicating successful authentication;
   obtaining new pulse data from the user during the access session;
   performing another comparison between the new pulse data from the user and the expected pulse data for the user during the access session; and
   generating another authentication result based on the comparison between the new pulse data and the expected pulse data to further authenticate the user during the access session.

10. The method as in claim 9, further comprising:
    maintaining the access session to provide the user with further access to the computerized resource when the other authentication result has a successful authentication value, and
    terminating the access session to prevent the user from further accessing the computerized resource when the other authentication result has an unsuccessful authentication value.

11. The method as in claim 1 wherein generating the authentication result includes:
    providing, as the authentication result, a control signal to control user access of the computerized resource, the control signal being based on (i) the comparison between the current pulse data and the expected pulse data and (ii) a result of a facial recognition operation.

12. The method as in claim 1, further comprising:
after the user has accessed the computerized resource in response to the authentication result indicating successful user authentication, generating a series of new authentication results based on subsequent pulse data comparisons and providing the user with continuous access to the computerized resource based on the series of new authentication results.

13. The method as in claim 12 wherein providing the user with continuous access to the computerized resource includes:
after the user has accessed the computerized resource for a continuous period of time based on the series of new authentication results, preventing further access to the computerized resource in response to a failure to receive further current pulse data.

14. An electronic apparatus to perform an authentication operation, the electronic apparatus comprising:
an interface;
memory; and
a controller coupled to the interface and the memory, the controller being constructed and arranged to:
obtain current pulse data from a user through the interface, perform a comparison between the current pulse data and expected pulse data from the memory, and
generate an authentication result based on the comparison between the current pulse data and the expected pulse data, the authentication result being constructed and arranged to control user access to a computerized resource;
wherein the controller, when performing the comparison between the current pulse data and the expected pulse data, is constructed and arranged to:
retrieve previously obtained cardiac pulse data of the user from a cardiac pulse waveform database which stores multiple pulse data entries, each pulse data entry including (i) pulse data and (ii) a timestamp,
identify a set of pulse waveform adjustments from the pulse data entries, and
generate, as at least part of the expected pulse data, measurements of an expected cardiac pulse waveform for the user based on (i) pulse data of particular pulse data entries stored in the cardiac pulse waveform database, (ii) the set of pulse waveform adjustments, and (iii) current time information.

15. The electronic apparatus as in claim 14 wherein the controller, when obtaining the current pulse data from the user through the interface, is constructed and arranged to:
receive, through the interface, an electronic input signal from an electronic input device while the electronic input device is physically separated from the user to take a current pulse measurement from the user in a non-contact manner, and
derive the current pulse data from the electronic input signal.

16. The electronic apparatus as in claim 15 wherein the electronic input device is a digital camera;
wherein, when the controller receives the electronic input signal from the electronic input device, the controller is constructed and arranged to capture video data while the user is within a field of view of the digital camera; and
wherein, when the controller derives the current pulse data from the electronic input signal, the controller is constructed and arranged to perform a set of computational operations on the video data to identify, as at least part of the current pulse data, a current cardiac pulse waveform of the user from the user's face.

17. The electronic apparatus as in claim 14 wherein the controller, when generating the authentication result based on the comparison between the current pulse data and the expected pulse data, is constructed and arranged to:
output, as the authentication result, a risk score based on a set of risk factors, a result of the comparison between the current pulse data and the expected pulse data being one of the set of risk factors.

18. The electronic apparatus as in claim 17 wherein the controller is further constructed and arranged to:
grant access to the computerized resource when the risk score exceeds a predefined threshold, and
deny access to the computerized resource when the risk score does not exceed the predefined threshold.

19. The electronic apparatus as in claim 14 wherein the controller, when generating the authentication result, is constructed and arranged to:
provide, as the authentication result, a control signal to control user access of the computerized resource, the control signal being based on (i) the comparison between the current pulse data and the expected pulse data and (ii) a result of a facial recognition operation.

20. A computer program product having a non-transitory computer readable medium which stores a set of instructions for performing an authentication operation, the set of instructions causing a computer to perform a method of:
obtaining current pulse data from a user;
performing a comparison between the current pulse data from the user and expected pulse data for the user; and
generating an authentication result based on the comparison between the current pulse data and the expected pulse data, the authentication result being constructed and arranged to control user access to a computerized resource;
wherein performing the comparison between the current pulse data from the user and the expected pulse data for the user includes:
retrieving previously obtained cardiac pulse data of the user from a cardiac pulse waveform database which stores multiple pulse data entries, each pulse data entry including (i) pulse data and (ii) a timestamp,
identifying a set of pulse waveform adjustments from the pulse data entries, and
generating, as at least part of the expected pulse data, measurements of an expected cardiac pulse waveform for the user based on (i) pulse data of particular pulse data entries stored in the cardiac pulse waveform database, (ii) the set of pulse waveform adjustments, and (iii) current time information.

21. The computer program product as in claim 20 wherein obtaining the current pulse data from the user includes:
receiving an electronic input signal from an electronic input device which is physically separated from the user to take a current pulse measurement from the user in a non-contact manner, and
deriving the current pulse data from the electronic input signal.

22. The computer program product as in claim 21 wherein the electronic input device is a digital camera;
wherein receiving the electronic input signal from the electronic input device includes capturing video data while the user is within a field of view of the digital camera; and wherein deriving the current pulse data from the electronic input signal includes performing a set of blind source separation operations on the video data to identify, as at least part of the current pulse data, a current cardiac pulse waveform of the user from the user's face.

23. The computer program product as in claim 20 wherein generating the authentication result based on the comparison between the current pulse data and the expected pulse data includes:

outputting, as the authentication result, a risk score based on a set of risk factors, a result of the comparison between the current pulse data and the expected pulse data being one of the set of risk factors.

24. The computer program product as in claim 23 wherein the method further comprises:

granting access to the computerized resource when the risk score exceeds a predefined threshold, and denying access to the computerized resource when the risk score does not exceed the predefined threshold.

25. The computer program product as in claim 20 wherein generating the authentication result includes:

providing, as the authentication result, a control signal to control user access of the computerized resource, the control signal being based on (i) the comparison between the current pulse data and the expected pulse data and (ii) a result of a facial recognition operation.

* * * * *